US012070539B2

(12) United States Patent
Rovatti et al.

(10) Patent No.: US 12,070,539 B2
(45) Date of Patent: Aug. 27, 2024

(54) EXTRACORPOREAL BLOOD TREATMENT METHOD

(71) Applicant: GAMBRO LUNDIA AB, Lund (SE)

(72) Inventors: Paolo Rovatti, Finale Emilia (IT); Katty Ferrari, Finale Emilia (IT)

(73) Assignee: GAMBRO LUNDIA AB, Lund (SE)

( * ) Notice: Subject to any disclaimer, the term of this patent is extended or adjusted under 35 U.S.C. 154(b) by 170 days.

(21) Appl. No.: 17/948,833

(22) Filed: Sep. 20, 2022

(65) Prior Publication Data

US 2023/0014488 A1  Jan. 19, 2023

Related U.S. Application Data

(63) Continuation of application No. 16/956,958, filed as application No. PCT/EP2018/068214 on Jul. 5, 2018, now Pat. No. 11,471,576.

(30) Foreign Application Priority Data

Dec. 28, 2017  (EP) ..................... 17210994

(51) Int. Cl.
*A61M 1/16* (2006.01)
*A61M 1/30* (2006.01)
(Continued)

(52) U.S. Cl.
CPC ........ *A61M 1/1656* (2013.01); *A61M 1/1605* (2014.02); *A61M 1/165* (2014.02);
(Continued)

(58) Field of Classification Search
CPC .. A61M 1/1605; A61M 1/165; A61M 1/1656; A61M 1/303; A61M 1/34; A61M 1/3643; A61M 2205/50; A61M 60/113
See application file for complete search history.

(56) References Cited

U.S. PATENT DOCUMENTS 4,718,022 A   1/1988   Cochran
4,731,731 A   3/1988   Cochran
(Continued)

FOREIGN PATENT DOCUMENTS

EP        1776971 A1      4/2007
KR    10-2010-0005210 A   1/2010
(Continued)

OTHER PUBLICATIONS

International Search Report; International Application No. PCT/EP2018/068214; mailed Sep. 24, 2018; 3 Pages.
(Continued)

*Primary Examiner* — Dirk R Bass
(74) *Attorney, Agent, or Firm* — K&L Gates LLP

(57) ABSTRACT

An extracorporeal blood treatment apparatus comprises: a blood treatment device (2) comprising a blood chamber (3) and a fluid chamber (4) separated from one another by a semipermeable membrane (5); an extracorporeal blood circuit (17) comprising a blood withdrawal line (6) connected to an inlet port (3a) of the blood chamber (3) and a blood return line (7) connected to an outlet port (3b) of the blood chamber (3); a blood pump (21) configured to be coupled to the blood withdrawal line (6); a hydraulic circuit (100) connectable to the fluid chamber (4), wherein the hydraulic circuit (100) comprises a fluid preparation device (9) connected to a water network (14) and configured to dilute concentrates in water to prepare a treatment fluid; a control unit (12) connected to the preparation device (9) and to the blood pump (21). The control unit (12) is configured to execute the following procedure: setting the hydraulic circuit (100) so that the fluid preparation device (9) bypasses the fluid chamber (4); controlling the fluid preparation device (9) to prepare the treatment fluid while bypassing the fluid chamber (4); and simultaneously controlling the blood
(Continued)

pump (21) to perform pure ultrafiltration of a patient (P) connected to the extracorporeal blood circuit (17).

20 Claims, 8 Drawing Sheets

(51) Int. Cl.
  *A61M 1/34* (2006.01)
  *A61M 1/36* (2006.01)
  *A61M 60/113* (2021.01)
(52) U.S. Cl.
  CPC ............. *A61M 1/303* (2014.02); *A61M 1/34* (2013.01); *A61M 1/3643* (2013.01); *A61M 60/113* (2021.01); *A61M 2205/50* (2013.01)

(56) References Cited

U.S. PATENT DOCUMENTS

| | | |
|---|---|---|
| 4,739,492 A | 4/1988 | Cochran |
| 2009/0107335 A1 | 4/2009 | Wilt et al. |
| 2010/0130906 A1 | 5/2010 | Balschat et al. |

FOREIGN PATENT DOCUMENTS

| | | |
|---|---|---|
| KR | 10-2010-0129797 A | 12/2010 |
| KR | 10-2015-0127946 A | 11/2015 |
| WO | WO 94/08641 A1 | 4/1994 |
| WO | WO 9625214 A1 | 8/1996 |
| WO | WO0006217 A1 | 2/2000 |
| WO | WO 2012162515 A2 | 11/2012 |
| WO | WO 2014097115 A2 | 6/2014 |
| WO | WO 2014097115 A3 | 6/2014 |
| WO | WO 2014173747 A1 | 10/2014 |
| WO | WO 2015183976 A2 | 12/2015 |
| WO | WO 2015184033 A2 | 12/2015 |

OTHER PUBLICATIONS

Written Opinion of the International Searching Authority; International Application No. PCT/EP2018/068214; mailed Sep. 24, 2018; 5 Pages.

Extended European Search Report issued in related EP Application No. 17210994.4 mailed Jun. 27, 2018—5 Pages.

Korean Office Action from corresponding Korean Patent Application No. 10-2020-7021851, mailed Feb. 23, 2023.

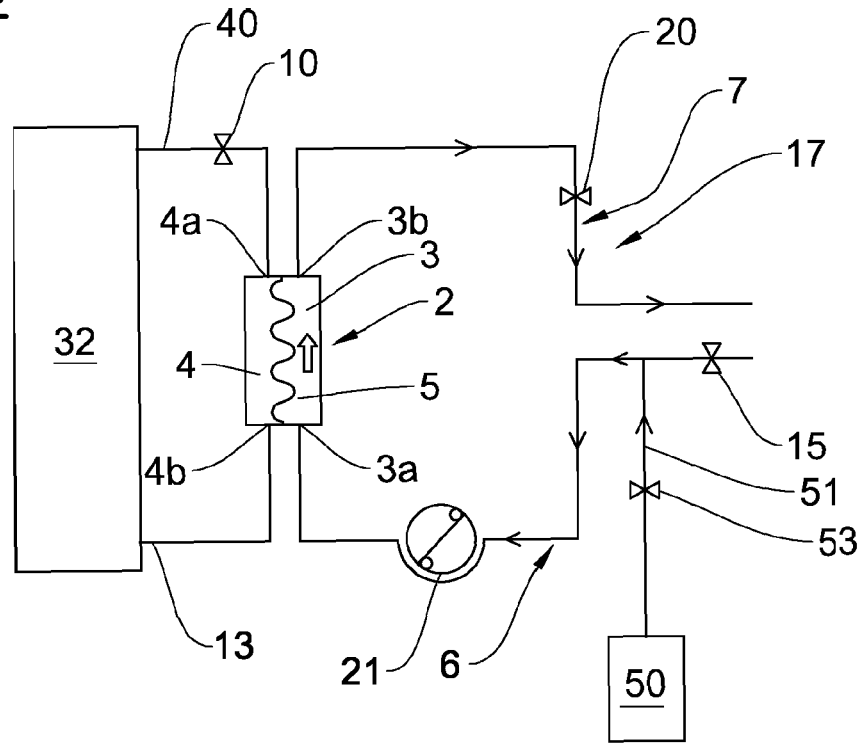
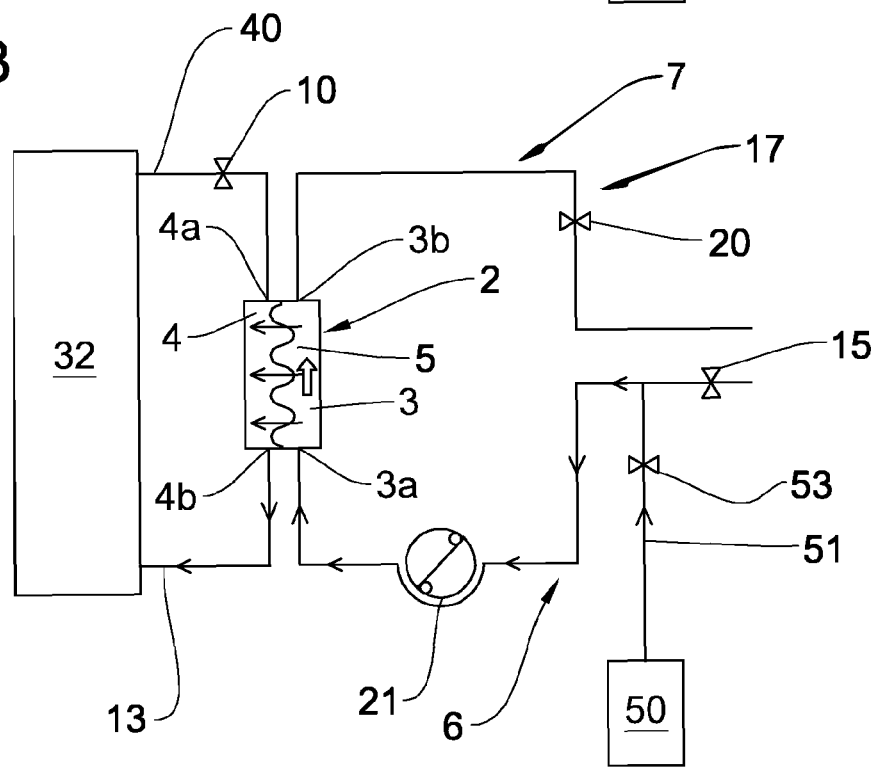

EXTRACORPOREAL BLOOD TREATMENT METHOD

PRIORITY CLAIM

The present application is continuation of U.S. Ser. No. 16/956,958, filed Jun. 22, 2020, entitled "Extracorporeal Blood Treatment Apparatus", which is a National Phase of International Application No. PCT/EP2018/068214, filed Jul. 5, 2018, which claims priority to EP Application No. 17210994.4, filed Dec. 28, 2017, the entire contents of each of which are incorporated herein by reference and relied upon.

DESCRIPTION

Field of the Invention

The present invention relates to an extracorporeal blood treatment apparatus. The extracorporeal blood treatment apparatus according to the invention is of the kind that could comprise a device for on-line preparation of a treatment fluid. The described embodiment also concerns a method for controlling an extracorporeal blood treatment apparatus.

Extracorporeal blood treatment involves removing blood from a patient, treating the blood externally to the patient, and returning the treated blood to the patient. Extracorporeal blood treatment is typically used to extract undesirable matter or molecules from the patient's blood and/or to add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood, to maintain an acid/base balance or to remove excess body fluids, for example.

Extracorporeal blood treatment is typically accomplished by removing the blood from the patient in e.g. a continuous flow, introducing the blood into a primary chamber, also referred to as blood chamber, of a treatment unit (such as a dialyzer or an hemo-filter) where the blood is allowed to flow past a semi-permeable membrane. The semi-permeable membrane selectively allows matter in the blood to cross the membrane from the primary chamber into a secondary chamber and also selectively allows matter in the secondary chamber to cross the membrane into the blood in the primary chamber, depending on the type of treatment.

A number of different types of extracorporeal blood treatments may be performed. In an ultrafiltration (UF) treatment, undesirable fluid is removed from the blood by convection across the membrane into the secondary chamber. In a hemofiltration (HF) treatment, the blood flows past the semipermeable membrane as in UF (where waste and undesirable fluid are removed) and desirable matter is added to the blood, typically by dispensing a fluid into the blood either before and/or after it passes through the treatment unit and before it is returned to the patient. In a hemodialysis (HD) treatment, a secondary fluid containing desirable matter is introduced into the secondary chamber of the treatment unit. Undesirable matter from the blood crosses the semi-permeable membrane into the secondary fluid by diffusion and desirable matter from the secondary fluid crosses the membrane into the blood. In a hemodiafiltration (HDF) treatment, blood and secondary fluid exchange matter as in HD, and, in addition, matter is added to the blood, typically by dispensing a fluid into the treated blood (infusion) either before and/or after it passes through the treatment unit and before its return to the patient as in HF.

In order to perform extracorporeal blood treatment therapies involving the use of treatment fluid prepared by the device for on-line preparation of a treatment fluid, the device must be switched on and parameters of the treatment fluid (like conductivity, temperature and flow rate) must be adjusted before starting the treatment.

BACKGROUND

Document WO2015184033A2 discloses a method for treating dialysate solutions used in sorbent dialysis wherein a small volume of dialysate is continuously regenerated. To initially prepare dialysate for circulation through dialysate circuit, the dialysate circuit is primed with a precursor dialysate solution in a supply container. After completing the introduction of the precursor dialysate solution into the dialysate circuit, valves are opened so that dialysate can flow between the dialyzer and the dialysate circuit concurrent with blood flow from and to the patient through the dialyzer to support a dialysis treatment. Dialysate is made in-situ. A supply of saline in the form of a saline bag is used to prime the blood circuit. Sterile saline can also be used to prime the dialysate circuit.

Document U.S. Pat. No. 4,718,022A discloses a dialysis machine having a control circuit which detects changes in input water temperature and compensates the water heater. The dialysis machine proceeds to produce dialysate during the priming operation of hydraulic circuit. In the priming mode, however, the dialysate being produced is either internally or externally recirculated so as to bypass the artificial kidney. Once the dialysis machine determines that the dialysate is being produced at the selected temperature, flow rate and pressure, the operator may be notified that dialysis may be commenced. Priming of blood circuit with saline is also performed.

Document WO9625214A1 discloses a machine for conducting dialysis of body fluids of a patient which is suitable for use in home environment. This document discloses to prepare dialysate in a tank of a dialysis preparation module, to check the integrity of the dialysate circuit and to prime the extracorporeal blood circuit. Water is back-filtered across the membrane of the dialyzer into the extracorporeal circuit. The automatic priming process may be implemented as a sequence of steps pre-, during, and post-dialysate preparation. Priming of the extracorporeal circuit with saline is also disclosed.

Document WO0006217A1 discloses an apparatus and method for controlling ultrafiltration and a method for priming blood compartment of a hemodialyzer. WO0006217A1 discloses to produce on-line a dialysate solution in the hydraulic circuit by mixing concentrates in a water stream. Before beginning a dialysis treatment, dialysate flow by-pass the hemodialyzer flowing through rinse block. Priming of blood lines and compartment is achieved by urging passage of dialysate from the dialysate compartment to the blood compartment and thus eliminates the need to consume isotonic saline.

Known apparatuses and methods as described above require time to perform dialysis on-line fluid preparation. Specifically though not exclusively, fluid preparation in extracorporeal blood treatment machines for ICHD treatments (In Center Haemo-Dialysis) is critical.

When a patient reaches the clinic with excessive fluid to be removed urgently, he has to wait for on-line fluid preparation and for priming of the circuits before starting the treatment. Indeed, only once dialysis fluid is at the proper conductivity and temperature, the blood circuit can be primed. This implies tens of minutes to start any fluid removal from patient and/or treatment and this causes patient discomfort and pain and stress for the clinic staff because of the emergency situation.

SUMMARY OF THE INVENTION

In view of the above, it is an object of the present invention to provide an extracorporeal blood treatment apparatus and method of controlling an extracorporeal blood treatment apparatus which are able to obviate at least some of the described drawbacks of the prior art.

It is a further object of the present invention to provide an apparatus and a method which are able to shorten the waiting time (time to treatment) for the patient.

It is a further object of embodiments of the present invention to provide an apparatus and a method which are able to reduce the physical stress of the patients.

It is a further object of embodiments of the present invention to provide an apparatus and a method which are able to provide a better treatment to patients, in particular though not exclusively, to patients in severe or critical conditions.

It is a further object of embodiments of the present invention to provide an apparatus and a method which are able to increase the therapy offer of the clinic (number of treated patients per time unit).

It is a further object of embodiments of the present invention to provide an apparatus and a method which are able to optimize the efficiency of the clinic and the exploitation of available apparatuses for extracorporeal treatment of blood.

At least one of the above objects is substantially achieved by performing online preparation of the treatment fluid simultaneously with pure ultrafiltration of the patient, and optionally with priming, while the blood treatment device is in by-pass, then starting dialysis when the treatment fluid is ready. Pure ultrafiltration means ultrafiltration without simultaneous dialysis (fluid removal only in the blood treatment device and no hemodialysis or hemofiltration).

Aspects of the invention are disclosed in the following.

In accordance with a $1^{st}$ independent aspect, an extracorporeal blood treatment apparatus comprises:
  a blood treatment device comprising a blood chamber and a fluid chamber separated from one another by a semipermeable membrane;
  an extracorporeal blood circuit comprising a blood withdrawal line connected to an inlet port of the blood chamber and a blood return line connected to an outlet port of the blood chamber;
  a blood pump configured to be coupled to the extracorporeal blood circuit to circulate blood in the extracorporeal blood circuit, in particular configured to be coupled to the blood withdrawal line;
  a hydraulic circuit including a main line connectable to an inlet port of the fluid chamber and/or to the extracorporeal blood circuit and an effluent line connected to an outlet port of the fluid chamber, the main line being connectable to a water network to receive water, wherein the hydraulic circuit comprises a fluid preparation device configured to dilute concentrates in water flowing in the main line to prepare a treatment fluid having set conductivity and/or set ion concentration;
  an ultrafiltration device to ultrafilter liquid from the blood chamber towards the fluid chamber of the blood treatment device and to the effluent line;
  a control unit connected to the preparation device, to the ultrafiltration device and to the blood pump;
  wherein the control unit is configured to execute the following procedure:
  setting the hydraulic circuit so that a fluid prepared through the fluid preparation device and not having the set conductivity and/or the set ion concentration bypasses the fluid chamber and is not infused in the extracorporeal blood circuit;
  controlling the fluid preparation device to change a conductivity and/or an ion concentration of the fluid not having the set conductivity and/or the set ion concentration to prepare the treatment fluid having the set conductivity and/or the set ion concentration while bypassing the fluid chamber and not infusing the fluid in the extracorporeal blood circuit; and
  simultaneously controlling the ultrafiltration device to perform pure ultrafiltration of fluid from the extracorporeal blood of a patient connected to the extracorporeal blood circuit.

In accordance with a $2^{nd}$ independent aspect, a method for controlling an extracorporeal blood treatment apparatus, particularly of the type in accordance with the $1^{st}$ aspect, comprises:
  setting a hydraulic circuit so that a fluid prepared through a fluid preparation device and not having a set conductivity and/or a set ion concentration bypasses a fluid chamber of a blood treatment device and is not infused in the extracorporeal blood circuit;
  controlling the fluid preparation device to change a conductivity and/or an ion concentration of the fluid not having the set conductivity and/or the set ion concentration to prepare the treatment fluid having the set conductivity and/or the set ion concentration while bypassing the fluid chamber and not infusing the fluid in the extracorporeal blood circuit; and
  simultaneously controlling an ultrafiltration device of the extracorporeal blood treatment apparatus to perform pure ultrafiltration of fluid from the extracorporeal blood of a patient connected to the blood withdrawal line and to a blood return line of an extracorporeal blood circuit.

In accordance with a further independent aspect, an extracorporeal blood treatment apparatus is provided comprising:
  a blood treatment device comprising a blood chamber and a fluid chamber separated from one another by a semipermeable membrane;
  an extracorporeal blood circuit comprising a blood withdrawal line connected to an inlet port of the blood chamber and a blood return line connected to an outlet port of the blood chamber;
  a blood pump configured to be coupled to the extracorporeal blood circuit to circulate blood in the extracorporeal blood circuit, in particular configured to be coupled to the blood withdrawal line;
  a hydraulic circuit including a main line connectable to an inlet port of the fluid chamber and/or to the extracorporeal blood circuit and an effluent line connected to an outlet port of the fluid chamber, the main line being connectable to a water network to receive water, wherein the hydraulic circuit comprises a fluid preparation device configured to dilute concentrates in water flowing in the main line to prepare a treatment fluid having set conductivity and/or set ion concentration;

an ultrafiltration device to ultrafilter liquid from the blood chamber towards the fluid chamber of the blood treatment device and to the effluent line;

at least one priming fluid, e.g. saline, reservoir connected to the extracorporeal blood circuit or to the blood treatment device or to the hydraulic circuit;

a control unit connected to the preparation device, to the ultrafiltration device and to the blood pump;

wherein the control unit is configured to execute the following procedure:

setting the hydraulic circuit so that a fluid prepared through the fluid preparation device and not having the set conductivity and/or the set ion concentration bypasses the fluid chamber and is not infused in the extracorporeal blood circuit;

controlling the fluid preparation device to change a conductivity and/or an ion concentration of the fluid not having the set conductivity and/or the set ion concentration to prepare the treatment fluid having the set conductivity and/or the set ion concentration while bypassing the fluid chamber and not infusing the fluid in the extracorporeal blood circuit; and simultaneously, in a priming configuration, priming the extracorporeal blood circuit with a priming fluid before connecting the patient and while the fluid preparation device is preparing the treatment fluid.

In a $3^{rd}$ aspect according to any of the previous aspects, in a priming configuration, the apparatus comprises at least one priming fluid, e.g. saline, source, e.g. a reservoir, connected to the extracorporeal blood circuit or to the blood treatment device or to the hydraulic circuit.

In a $4^{th}$ aspect according any of the previous aspects, the control unit is configured to execute the following procedure or the method comprises: in a priming configuration, priming the extracorporeal blood circuit with a priming fluid before connecting the patient and while the fluid preparation device is preparing the treatment fluid, in particular the priming fluid source being connected to the extracorporeal blood circuit.

In a $5^{th}$ aspect according to any the previous aspect 3 or 4, the control unit is configured to execute the following procedure or the method comprises: in a priming configuration, priming the fluid chamber and optionally at least part of the hydraulic circuit with the priming fluid by pushing the priming fluid through the membrane from the blood chamber into the fluid chamber before connecting the patient and while the fluid preparation device is preparing the treatment fluid.

In an alternative $5^{th}$ aspect according to any the previous aspect 3 or 4, the control unit is configured to execute the following procedure or the method comprises: in a priming configuration, priming the fluid chamber and optionally at least part of the hydraulic circuit with a priming fluid from an auxiliary priming fluid source, e.g. a container, the auxiliary priming fluid source being connected to the blood treatment device or to the hydraulic circuit and being separated by the semipermeable membrane from the extracorporeal blood circuit. Optionally, the auxiliary priming fluid source being connected via a tubing directly to the inlet port of the fluid chamber.

In a $6^{th}$ aspect according to any of the previous aspects from 1 to 5, the control unit is configured to execute the following procedure or the method comprises: in a treatment configuration, connecting the fluid preparation device to the fluid chamber and/or to the extracorporeal blood circuit when the treatment fluid having the set conductivity and/or the set ion concentration is ready for treating the patient blood.

In a $7^{th}$ aspect according to any of the previous aspects from 1 to 6, the control unit is configured to execute the following procedure or the method comprises: in a treatment configuration, starting a hemodialysis treatment or a hemofiltration treatment or a hemodiafiltration treatment on the patient when the treatment fluid having the set conductivity and/or the set ion concentration is ready.

In an $8^{th}$ aspect according to any of the previous aspects from 1 to 7, the main line of the hydraulic circuit comprises a valve operatively placed between the preparation device and the inlet port of the fluid chamber.

In a $9^{th}$ aspect according to the previous aspect 8, the control unit is connected to the valve and is configured to execute the following procedure: in a treatment fluid preparation configuration, closing the valve to set the fluid flowing in the main line downstream the fluid preparation device to bypass the fluid chamber.

In a $10^{th}$ aspect according to the previous aspect 4, in the priming configuration, priming the extracorporeal blood circuit includes controlling the blood pump while the priming fluid source is connected to the extracorporeal blood circuit to pump the priming fluid in the extracorporeal blood circuit and to prime the extracorporeal blood circuit with the priming fluid.

Optionally, in the priming configuration the extracorporeal blood circuit is directly connected to the fluid chamber through a tubing. Optionally, the blood withdrawal line is directly connected to the fluid chamber, optionally to the inlet port of the fluid chamber. Optionally, the blood pump circulates the priming fluid along a reverse circulating direction. The blood pump pumps the priming fluid into the fluid chamber through the tubing, in order to prime said fluid chamber and optionally at least part of the hydraulic circuit. Optionally, in the priming configuration, the priming fluid flows through the blood chamber, out of the inlet port of the blood chamber and then into the fluid chamber. Optionally, the priming fluid exits from the outlet of the fluid chamber and flows into the effluent line.

In an $11^{th}$ aspect according to any of the previous aspects 3, 4 or 10, the apparatus comprises a safety valve placed on the blood return line, the control unit being connected to the safety valve, and an arterial clamp placed on the blood withdrawal line, the control unit being connected to the arterial clamp.

In a $12^{th}$ aspect according to the previous aspect 11, in the priming configuration, priming the extracorporeal blood circuit includes a first phase of priming the blood withdrawal line and the blood return line activating the blood pump to circulate priming fluid along a reverse circulating direction, in the extracorporeal blood circuit and keeping the arterial clamp and the safety valve open and a second, optionally subsequent, phase of closing the safety valve and activating the blood pump to circulate the priming fluid in the blood circuit along a normal circulating direction, thereby pushing the priming fluid through the membrane and priming the fluid chamber with the priming fluid.

In a $13^{th}$ aspect according to the previous aspect 12, the apparatus comprises a drain in fluid communication with the fluid chamber and the second phase includes removing air from the fluid chamber through the drain.

In a $14^{th}$ aspect according to any of the previous aspects 8 or 9, the control unit is configured to execute the following procedure: in a treatment configuration, when the treatment fluid is ready in order to start a hemodialysis treatment or a hemofiltration treatment or a hemodiafiltration treatment on the patient, opening the valve to connect the fluid preparation device to the inlet port of the fluid chamber and/or to an infusion line for injecting substitution fluid in the blood circuit.

In a 15th aspect according to any of the previous aspects 1 to 14, a time interval for treatment fluid preparation is comprised between 15 min and 30 min.

In a 16th aspect according to any of the previous aspects from 1 to 15, a time interval for pure ultrafiltration is comprised between 10 min and 20 min.

In a 17th aspect according to any of the previous aspects 4, 5 or 6 to 16 when referring to aspect 4 or 5, a time interval for priming is comprised between 5 min and 10 min.

In a 18th aspect according to any of the previous aspects 1 to 17, a time to treatment from the start of the treatment fluid preparation to start the pure ultrafiltration is less than 10 min, optionally less than 5 min.

In a 19th aspect according to any of the previous aspects 1 to 18, the priming fluid is saline, in particular saline including a substantially isotonic liquid with no potassium and magnesium ions.

In a 20th aspect according to any of the previous aspects form 1 to 19, the treatment fluid comprises dialysis liquid including treatment amounts of at least sodium, magnesium and potassium.

In a 21st aspect according to any of the previous aspects from 1 to 20, concentrates comprises sodium chloride and/or calcium chloride and/or magnesium chloride and/or potassium chloride and/or bicarbonate.

In a 22nd aspect according to any of the previous aspects from 1 to 21, the fluid chamber comprises an inlet port and an outlet port, wherein the hydraulic circuit is connected to the inlet port and the outlet port of the fluid chamber.

In a 23rd aspect according to any of the previous aspects from 1 to 22, the fluid preparation device is connected to the inlet port of the fluid chamber.

In a 24th aspect according to any of the previous aspects from 1 to 23, an effluent line for waste fluid is connected to the outlet port of the fluid chamber.

In a 25th aspect according to any of the previous aspects from 1 to 24, an arterial clamp is placed on the blood withdrawal line.

In a 26th aspect according to any of the previous aspects from 1 to 25, the fluid preparation device comprises:
at least a first and a second concentrate sources,
a first and a second delivery lines for respectively connecting the first and a second concentrate sources to the main line; and a first and a second concentrate pumps configured to respectively act on the first and a second delivery lines to allow the metered mixing of water and concentrated solution in the main line.

In a 27th aspect according to any of the previous aspects from 1 to 26, the fluid preparation device comprises a conductivity or a ion concentration sensor placed in the main line arranged to sense conductivity or ion concentration of the treatment fluid downstream a concentrate dilution point, the control unit being connected to the conductivity or ion concentration sensor to receive a signal indicative of the conductivity or ion concentration of the fluid flowing in the main line.

In a 28th aspect according to the previous aspect, in the controlling of the fluid preparation device, the control unit is configured to:
receive, e.g. as input from an operator or from a memory, the set conductivity and/or the set ion concentration for the treatment fluid;
start injecting at least one concentrated solution in the main line to increase the conductivity or ion concentration of water flowing in the main line.

In a 29th aspect according to the previous aspect, in the controlling of the fluid preparation device, the control unit is further configured to:
check, by means of the conductivity or ion concentration sensor, whether the conductivity or ion concentration of the fluid flowing in the main line has a proper value for treatment of patient blood, a proper value being a value within a range around the set conductivity and/or the set ion concentration for the treatment fluid.

In a 30th aspect according to the previous aspect, the range around the set conductivity and/or the set ion concentration for the treatment fluid being less than +/−2 mS/cm, in particular less than +/−1 mS/cm, even more in particular less than 0.5 mS/cm.

In a 31st aspect according to any of the previous aspects from 1 to 30, the fluid preparation device comprises a temperature sensor placed in the main line arranged to sense the temperature of the treatment fluid optionally downstream a concentrate dilution point, the control unit being connected to the temperature sensor to receive a signal indicative of the temperature of the fluid flowing in the main line.

In a 32nd aspect according to the previous aspect, in the controlling of the fluid preparation device, the control unit is configured to:
receive, e.g. as input from an operator or from a memory, the set temperature for the treatment fluid;
start heating water and/or the fluid flowing in the main line.

In a 33rd aspect according to the previous aspect, in the controlling of the fluid preparation device, the control unit is further configured to:
check, by means of the temperature sensor, whether the temperature of the fluid flowing in the main line has a proper value for treatment of patient blood, a proper value being a value within a range around the set temperature for the treatment fluid.

In a 34th aspect according to the previous aspect, the range around the set temperature for the treatment fluid being less than +/−2° C., in particular less than +/−1° C., even more in particular less than 0.5° C.

In a 35th aspect according to any of the previous aspects from 1 to 34, in a treatment fluid preparation configuration, the control unit is configured to execute the procedure of setting the hydraulic circuit so that the fluid prepared through the fluid preparation device and not having the set conductivity and/or the set ion concentration bypasses the fluid chamber and is not infused in the extracorporeal blood circuit; and controlling the fluid preparation device to change a conductivity and/or an ion concentration of the fluid not having the set conductivity and/or the set ion concentration to prepare the treatment fluid having the set conductivity and/or the set ion concentration while bypassing the fluid chamber and not infusing the fluid in the extracorporeal blood circuit, wherein controlling the fluid preparation device includes start injecting at least one concentrate solution in water to rise water conductivity and/or ion concentration.

In a 36th aspect according to any of the previous aspects from 1 to 35, in a pure UF configuration, the control unit is configured to execute the procedure of setting the hydraulic circuit so that the fluid prepared through the fluid preparation device bypasses the fluid chamber and is not infused in the extracorporeal blood circuit; and controlling the ultrafiltration device to perform pure ultrafiltration of fluid from the extracorporeal blood of a patient connected to the extracorporeal blood circuit.

In a 37th aspect according to previous aspects 35 and 36, at least at the starting of the apparatus, the apparatus is configured (or the control unit configures the apparatus) simultaneously in the treatment fluid preparation configuration and in the pure UF configuration.

In a 38th aspect according to previous aspects 4 and 37, at least at the starting of the apparatus, the apparatus is configured (or the control unit configures the apparatus) simultaneously in the treatment fluid preparation configuration and in the priming configuration.

In a 39th aspect according to previous aspects 37 and 38, at least at the starting of the apparatus, the apparatus is configured (or the control unit configures the apparatus) simultaneously in the treatment fluid preparation configuration and in the priming configuration and thereafter, once priming is ended, the apparatus is switched to be configured (or the control unit configures the apparatus to be) simultaneously in the treatment fluid preparation configuration and in the pure UF configuration.

In a 40th aspect according to any of the previous aspects from 1 to 39, controlling the fluid preparation device to change a conductivity and/or an ion concentration of the fluid not having the set conductivity and/or the set ion concentration to prepare the treatment fluid comprises controlling the fluid preparation device to substantially continuously raising the conductivity and/or ion concentration of the fluid not having the set conductivity and/or the set ion concentration up to obtaining a fluid substantially having the set conductivity and/or the set ion concentration.

In a 41st aspect according to previous aspect 40, controlling the fluid preparation device to substantially continuously raising the conductivity and/or ion concentration includes starting and then continuing injecting into water a concentrate ion solution.

In a 42nd aspect according to any of the previous aspects, the apparatus comprises a fresh dialysis fluid container connected to the inlet port of the fluid chamber, the control unit being configured to additionally run an hemodyalisis treatment flowing fresh dialysis fluid in the fluid chamber and patient blood in the blood chamber simultaneously with the step of controlling the fluid preparation device to change a conductivity and/or an ion concentration of the fluid not having the set conductivity and/or the set ion concentration to prepare the treatment fluid having the set conductivity and/or the set ion concentration.

In a 43rd aspect according to any of the previous aspects, the apparatus comprises a fresh dialysis fluid container connected to the extracorporeal blood circuit, the control unit being configured to additionally run a hemofiltration treatment injecting fresh dialysis fluid in the extracorporeal blood simultaneously with the step of controlling the fluid preparation device to change a conductivity and/or an ion concentration of the fluid not having the set conductivity and/or the set ion concentration to prepare the treatment fluid having the set conductivity and/or the set ion concentration.

In a 44th aspect according to any of the previous aspects, connecting the patient after priming comprises: connecting the blood withdrawal line and the blood return line to the patient while an arterial clamp on the blood withdrawal line and a safety valve on the blood return line are closed; opening the arterial clamp and the safety valve and activating the blood pump according to the normal circulating direction, to progressively substituting the priming fluid in the line with blood.

In a 45th according to any of the previous aspects from 1 to 43rd, connecting the patient after priming comprises: connecting the blood withdrawal line to the patient while the blood return line is still connected to a priming fluid reservoir and an arterial clamp on the blood withdrawal line and a safety valve on the blood return line are closed; opening the arterial clamp and the safety valve and activating the blood pump according to the normal circulating direction, to progressively substituting the priming fluid in the line with blood and to collect the priming fluid in the priming fluid reservoir.

DESCRIPTION OF THE DRAWINGS

The following drawings relating to aspects of the invention are provided by way of non-limiting example:

FIGS. 2 to 5 show a schematic representation of the extracorporeal blood treatment apparatus of FIG. 1 in respective working conditions;

DETAILED DESCRIPTION

Figure 1:
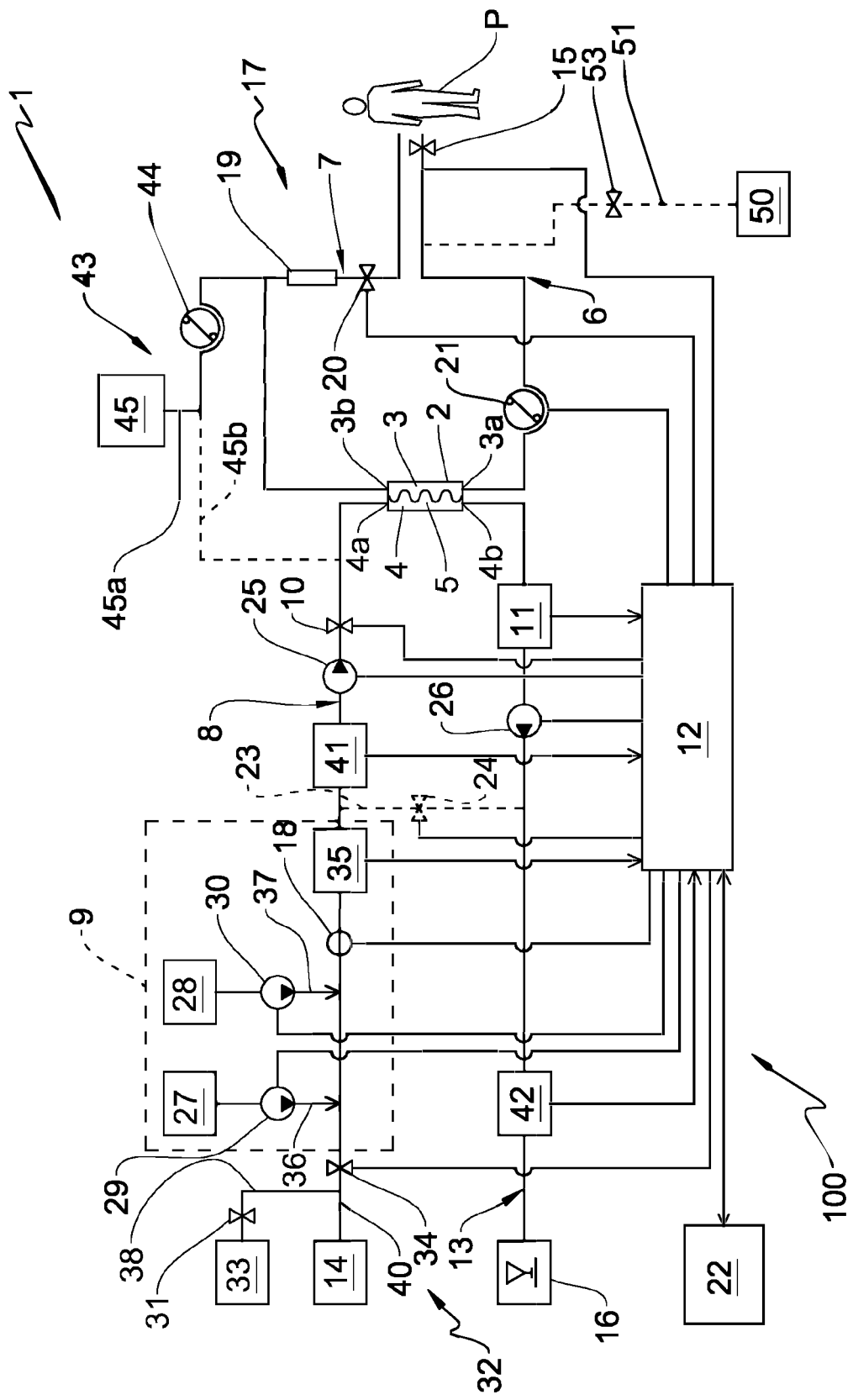
FIG. 1 represents an extracorporeal blood treatment apparatus made according to an illustrating embodiment.

With reference to the appended drawings, FIG. 1 shows a schematic representation of an extracorporeal blood treatment apparatus 1.

The apparatus 1 comprises one blood treatment device 2, for example a hemofilter, a hemodiafilter, a plasmafilter, a dialysis filter or other unit suitable for processing the blood taken from a vascular access of a patient P.

The blood treatment device 2 has a first compartment or blood chamber 3 and a second compartment or fluid chamber 4 separated from one another by a semipermeable membrane 5, for example of the hollow-fiber type or plate type. A blood withdrawal line 6 is connected to an inlet port 3a of the blood chamber 3 and is configured, in an operative condition of connection to the patient P, to remove blood from a vascular access device inserted, for example in a fistula on the patient P. A blood return line 7 connected to an outlet port 3b of the blood chamber 3 is configured to receive treated blood from the treatment unit 2 and to return the treated blood, e.g. to a further vascular access also connected to the fistula of the patient P. Note that various configurations for the vascular access device may be envisaged: for example, typical access devices include a needle or catheter inserted into a vascular access which may be a fistula, a graft or a central (e.g. jugular vein) or peripheral vein (femoral vein) and so on. The blood withdrawal line 6 and the blood return line 7 are part of an extracorporeal blood circuit 17 of the apparatus 1.

The extracorporeal blood circuit 17 and the blood treatment device 2 are usually disposable parts which are loaded onto a frame of a blood treatment machine, not shown.

The blood circuit 17 may also comprise one or more air separators 19: in the example of FIG. 1 a separator 19 is included at the blood return line 7, upstream of a safety valve 20. Of course other air separators may be present in the blood circuit 17, such as positioned along the blood withdrawal line 6. The safety valve 20 may be activated to close the blood return line 7 when, for example, for security reasons the blood return to the vascular access has to be halted.

As shown in FIG. 1, the apparatus 1 comprises at least a first actuator, in the present example a blood pump 21, which is part of said machine and operates at the blood withdrawal line 6, to cause movement of the blood removed from the patient P from a first end of the withdrawal line 6 connected to the patient P to the blood chamber 3. The blood pump 21 is, for example, positive displacement pump like a peristaltic pump, as shown in FIG. 1, which acts on a respective pump section of the withdrawal line 6. When rotated, e.g., clockwise, the blood pump 21 causes a flow of blood along the blood withdrawal line 6 towards the blood chamber 3 (see the arrows in FIG. 1 indicative of the blood flow along the withdrawal line 6).

It should be noted that for the purposes of the present description and the appended claims, the terms "upstream" and "downstream" may be used with reference to the relative positions taken by components belonging to or operating on the extracorporeal blood circuit. These terms are to be understood with reference to a blood flow direction from the first end of the blood withdrawal line 6 connected to the patient P towards the blood chamber 3 and then from the blood chamber 3 towards a second end of the blood return line 7 connected to the vascular access of the patient P.

The apparatus 1 further comprises a hydraulic circuit 100 cooperating with a blood circuit 17.

The hydraulic circuit 100 comprises a treatment fluid circuit 32 presenting at least one treatment fluid supply line 8, destined to transport a treatment fluid from at least one source towards the blood treatment device 2.

The treatment fluid circuit 32 further comprises at least one effluent line 13, destined for the transport of a dialysate liquid or waste fluid (spent treatment fluid and liquid ultrafiltered from the blood through a semipermeable membrane 5) from the blood treatment device 2 towards an evacuation zone, schematically denoted by 16 in FIG. 1.

The fluid supply line 8 is connected to an inlet port 4a of the fluid chamber 4. The effluent line 13 is connected to an outlet port 4b of the fluid chamber 4. The secondary chamber 4 is therefore connected to the hydraulic circuit 100.

The apparatus of above-described embodiment may also comprise a user interface 22 (e.g. a graphic user interface or GUI) and a control unit 12, i.e. a programmed/programmable control unit, connected to the user interface.

The control unit 12 may, for example, comprise one or more digital microprocessor units or one or more analog units or other combinations of analog units and digital units. Relating by way of example to a microprocessor unit, once the unit has performed a special program (for example a program coming from outside or directly integrated on the microprocessor card), the unit is programmed, defining a plurality of functional blocks which constitute means each designed to perform respective operations as better described in the following description.

In combination with one or more of the above characteristics, the extracorporeal blood treatment apparatus 1 may also comprise a closing device operating, for example, in the blood circuit 17 and/or in the treatment fluid circuit 32 and controllable between one first operating condition, in which the closing device allows a liquid to flow towards the blood treatment device 2, and a second operative position, in which the closing device blocks the passage of liquid towards the blood treatment device 2. In this case, the control unit 12 may be connected to the closing device and programmed to drive the closing device to pass from the first to the second operative condition, should an alarm condition have been detected. In FIG. 1 the closing device includes the safety valve 20 (e.g. a solenoid valve) controlled by the control unit 12 as described above. Obviously a valve of another nature, either an occlusive pump or a further member configured to selectively prevent and enable fluid passage may be used.

Additionally to the safety valve 20, the closing device comprises a bypass line 23 which connects the treatment fluid supply line 8 and the effluent line 13 bypassing the blood treatment device 2, and one or more fluid check members 24 connected to the control unit 12 for selectively opening and closing the bypass line 23. The components (bypass line 23 and fluid check members 24), which may be alternative or additional to the presence of the safety valve 20 are represented by a broken line in FIG. 1. The check members 24 on command of the control unit 12 close the fluid passage towards the blood treatment device 2 and connect the source directly with the effluent line 13 through the bypass line 23. Again with the aim of controlling the fluid passage towards the blood treatment device 2, a treatment fluid pump 25 and a dialysate pump 26 may be included, located respectively on the treatment fluid supply line 8 and on the effluent line 13 and also operatively connected to the control unit 12. A valve 10 is connected to the control unit 12 and is operatively placed between the preparation device 9 and the inlet port 4a of the fluid chamber 4. An arterial clamp 15 is connected to the control unit 12 and is operatively placed on the blood withdrawal line 6 close to the vascular access of the patient P.

The apparatus also comprises an ultrafiltration device to ultrafilter liquid from the blood chamber 3 towards the fluid chamber 4 of the blood treatment device 2 and to the effluent line 13. In the embodiment shown in FIG. 1, the ultrafiltration device may comprise the treatment fluid pump 25 and the dialysate pump 26 connected and controlled by the control unit 12, as will be explained further on.

The apparatus also comprises a treatment fluid preparation device 9 which may be of any known type, for example including one or more concentrate sources 27, 28 and respective concentrate pumps 29, 30 for the delivery, as well as at least a conductivity or ion concentration sensor 35. Of course other kinds of dialysis fluid preparation devices 9 might be equivalently used, having a single or further concentrate sources and/or a single or more pumps.

The extracorporeal blood treatment apparatus 1 may comprise various liquid sources (for example one or more water sources 14 from a water network, at least first and second concentrate sources 27, 28, one or more sources 33 of disinfectant liquids) connected to the main line 40 with respective first and second delivery lines 36, 37 and line 38, the apparatus may exhibit, at each delivery line, a respective check member (not all are shown) and, for example, comprising a valve member 31 and 34 and/or an occlusive pump.

The preparation device 9 may be any known system configured for on-line preparing dialysis fluid from water and concentrates (sodium chloride and/or calcium chloride and/or magnesium chloride and/or potassium chloride and/or bicarbonate). Through the preparation device 9, concentrates are diluted in water.

The treatment fluid supply line 8 fluidly connects the preparation device 9 for preparing treatment fluid to the blood treatment device 2. The preparation device 9 may be, for example, the one described in the U.S. Pat. No. 6,123,847 the content of which is herein incorporated by reference.

As shown, the treatment fluid supply line 8 connects the preparation device 9 for preparing treatment fluid to the blood treatment device 2 and comprises a main line 40 whose upstream end is intended to be connected to a source 14 of running water (water network). The valve 10 is part of the main line 40 of the hydraulic circuit 100.

Delivery line/s 36/37 is/are connected to this main line 40, the free end of which delivery line/s is/are intended to be in fluid communication (for example immersed) in a container/s 27, 28 for a concentrated saline solution each containing sodium chloride and/or calcium chloride and/or magnesium chloride and/or potassium chloride.

First and second concentrate pumps 29, 30 are arranged in the delivery lines 36, 37 in order to allow the metered mixing of water and concentrated solution in the main line 40. The concentrate pumps 29, 30 are driven on the basis of the comparison between 1) a target conductivity value for the mixture of liquids formed where the main line 40 joins the delivery lines 36, 37, and 2) the value of the conductivity of this mixture measured by means of the conductivity sensor 35 arranged in the main line 40 immediately downstream of the junction between the main line 40 and the delivery lines 36, 37.

Therefore, as mentioned, the treatment fluid comprises dialysis liquid which may contain, for example, ions of sodium, calcium, magnesium, and potassium and the preparation device 9 may be configured to prepare the treatment fluid on the basis of a comparison between a target conductivity value and/or set ion concentration and an actual conductivity value and/or actual ion concentration of the dialysis fluid measured by the conductivity sensor 35 of the device 9.

Concentrate pump/s (29, 30) work as regulating means which is configured to regulate the concentration of a specific substance, in particular an ionic substance, in the dialysis liquid. Generally it is advantageous to control the sodium concentration of the dialysis fluid.

The treatment fluid supply line 8 forms an extension of the main line 40 of the preparation device 9 for preparing treatment fluid. Arranged in this treatment fluid supply line, in the direction in which the liquid circulates, there are the first flow meter 41 and the treatment fluid pump 25.

The effluent line 13 may be provided with the dialysate pump 26 and a second flow meter 42. The first and second flow meters 41, 42 may be used to control (in a known manner) the fluid balance of a patient connected to the blood circuit 17 during a dialysis session.

A sensor 11 is provided on the effluent line 13, immediately downstream the blood treatment device 2, to measure a parameter value of the dialysate in the effluent line. The sensor 11 is a conductivity sensor which is configured to detect conductivity values of the dialysate downstream of the blood treatment device 2. Alternatively (or in combination) sensor 11 may include a concentration sensor configured for measuring the concentration of at least one substance in the dialysate, such as sodium concentration.

One or more infusion lines 43 may also be included, with respective infusion pumps 44 or flow regulation valves, the infusion lines being connected up to the blood return line 7 and/or the blood withdrawal line 6 and/or directly to the patient P. The liquid sources for the infusion lines may be pre-packaged bags 45 and/or liquids prepared by the apparatus itself.

In the example of FIG. 1, an infusion line 43 is shown directly connected to the blood return line 7, in particular to the air separator 19. The infusion line 43 may either receive infusion liquid from a pre-packaged bag 45 (solid line 45*a*) or from an online preparation trough branch 45*b* (dotted line).

Of course a pre-infusion line may be alternatively or additionally provided receiving the infusion liquid from a bag or from an online preparation device.

The extracorporeal blood treatment apparatus 1 comprises at least one priming fluid (e.g. saline, in particular saline including a substantially isotonic liquid with no potassium and magnesium ions) source 50, for example a container like a bag, connected or connectable to the blood withdrawal line 6 upstream of the blood pump 21. A priming fluid delivery line 51, optionally provided with a clamp 53, connects the priming fluid source 54 with a point of the blood withdrawal line 6 located between the arterial clamp 15 and the blood pump 21, or directly to the terminal part of the arterial blood line.

In a specific embodiment, the extracorporeal blood treatment apparatus comprises a further priming fluid (e.g. saline) source 54, for example a container like a bag, connected or connectable to either the hydraulic circuit or to the blood treatment device 2, particularly at the inlet port 4*a* of the fluid chamber 4.

Figure 10:
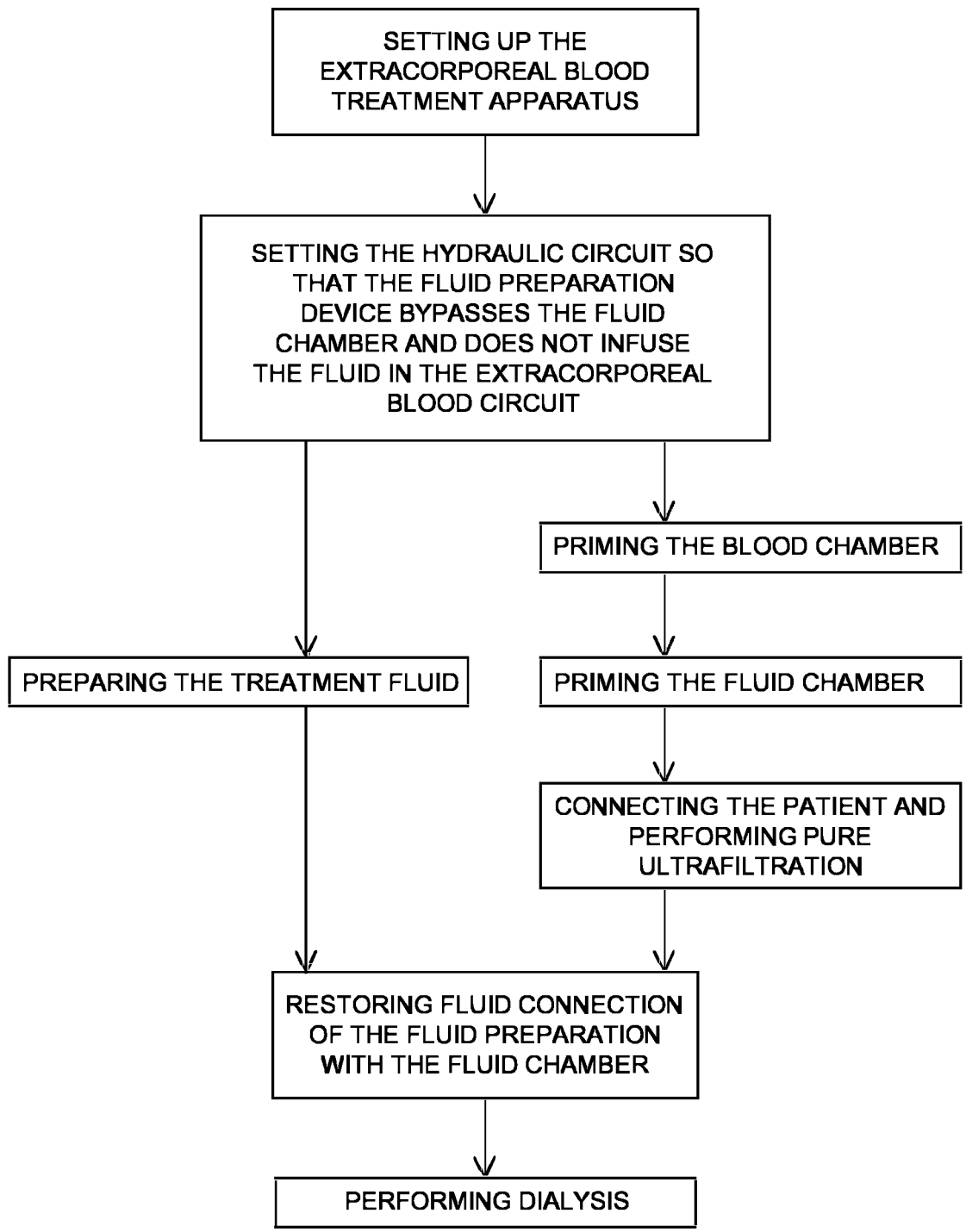
FIG. 10 is a flowchart of the method of the invention implemented by the apparatus of the invention.

Given the above description of a possible embodiment of extracorporeal blood treatment apparatus, thereafter the specific working of the apparatus is described, as schematically illustrated in the flowchart of FIG. 10.

According to the invention, when a patient P reaches the clinic, he has to wait only the time required to set up and prime the extracorporeal blood treatment apparatus 1. Then he is connected to the apparatus 1 to be submitted to pure ultrafiltration. Time to treatment from the start of the treatment fluid preparation to start the pure ultrafiltration may be less than 10 min.

At the starting of the apparatus 1, the apparatus 1 is configured, or the control unit 12 configures the apparatus 1 to be, simultaneously in the treatment fluid preparation configuration and in the priming configuration and thereafter, once priming is ended, the apparatus 1 is switched to be configured (or the control unit 12 configures the apparatus 1 to be) simultaneously in the treatment fluid preparation configuration and in the pure UF configuration.

In particular, the control unit 12 is configured to set the fluid preparation device 9 to bypass the fluid chamber 4 through the fluid check valve 10 (FIG. 1) which closes the fluid passage towards the blood treatment device 2 and connects the source directly with the effluent line 13 through the bypass line 23. FIG. 2 schematically shows this step (the treatment fluid circuit 32 is illustrated like a box). In a treatment fluid preparation configuration, the valve 10 is closed to set the fluid flowing in the main line 40 downstream the fluid preparation device 9 to bypass the fluid chamber 4. No fluid enters through the inlet port 4*a* of the fluid chamber 4. The patient P is not connected to the extracorporeal blood circuit 17.

The control unit 12 is configured to receive, e.g. as input from an operator or from a memory, the set conductivity and/or the set ion concentration for the treatment fluid and to start injecting at least one concentrated solution in the main line 40 to increase the conductivity or ion concentration of water flowing in the main line 40. The control unit checks, by means of the conductivity or ion concentration sensor 35, whether the conductivity or ion concentration of the fluid flowing in the main line 40 has a proper value for treatment of patient blood. The proper value is a value within a range around the set conductivity and/or the set ion concentration for the treatment fluid. The range around the set conductivity and/or the set ion concentration for the treatment fluid may be less than +/−2 mS/cm, in particular less than +/−1 mS/cm, even more in particular less than 0.5 mS/cm. The apparatus 1 continuously raises the conductivity and/or ion concentration of the fluid (by continuing injecting into water the concentrate ion solution) up to obtaining a fluid substantially having the set conductivity and/or the set ion concentration.

A temperature sensor 18 is placed in the main line 40 and it is connected to the control unit 12. The temperature sensor 18 is arranged to sense the temperature of the treatment fluid downstream a concentrate dilution point. The control unit 12 receives, e.g. as input from an operator or from the memory, a set temperature for the treatment fluid and starts heating water and/or the fluid flowing in the main line 40. In particular, the control unit 12 checks, by means of the temperature sensor 18, whether the temperature of the fluid flowing in the main line 40 has a proper value for treatment of patient blood. The proper value is a value within a range around the set temperature for the treatment fluid. The range around the set temperature for the treatment fluid may be less than +/−2° C., in particular less than +/−1° C., even more in particular less than 0.5° C. The control unit 12 controls the fluid preparation device 9, in particular concentrate pumps 29, 30 and valve members 31 and 34, to prepare the treatment fluid while the fluid preparation device 9 bypasses the fluid chamber 4 and is not infused in the extracorporeal blood circuit. The treatment fluid not having the set conductivity and/or the set ion concentration keeps on flowing through the bypass line 23 and into the effluent line 13 until the parameters of the treatment fluid, like conductivity and/or ion concentration, are correct. The fluid prepared through the treatment fluid preparation device 9 and not having the set conductivity and/or the set ion concentration bypasses the fluid chamber 4 and is not infused in the extracorporeal blood circuit 17.

The fluid preparation device 9 changes the conductivity and/or the ion concentration of the fluid not having the set conductivity and/or the set ion concentration to prepare the treatment fluid having the set conductivity and/or the set ion concentration.

Meanwhile (FIG. 2), the priming fluid source 50 is connected to the blood withdrawal line 6 and the (manual) clamp 53 is open to allow the priming fluid to flow into the blood withdrawal line 6. In a priming configuration and in a first phase, the control unit 12 drives the blood pump 21 to pump the priming fluid through the blood withdrawal line 6, the blood chamber 3 and the blood return line 7, in order to prime the blood chamber 3 and the blood circuit 17. Safety valve 20 is open and priming fluid circulates along a normal circulating direction and exits the blood return line 7 and then it is evacuated in a drain collecting bag or through the machine drain.

In a first priming with back-filtration embodiment, once priming of the blood chamber 3 is performed and while preparation of the treatment fluid still runs, the control unit 12 controls the safety valve 20 to close it. The control unit 12 keeps on driving the blood pump 21 to pump the priming fluid through the blood withdrawal line 6 and the blood chamber 3. Since passage through the blood return line 7 is prevented by the safety valve 20, priming fluid is pushed across the membrane 5 from the blood chamber 3 into the fluid chamber 4 (FIG. 3). Priming fluid than exits from the outlet 4b of the fluid chamber 4 and into the effluent line 13. The control unit 12 controls the dialysate pump 26 to pump priming fluid into evacuation zone 16. This way, the fluid chamber 4 is primed and air may be removed through the drain of the machine or a drain bag. A time interval "$\Delta T_{pr}$" for priming of blood and fluid chambers may be 5 min.

Figure 6:
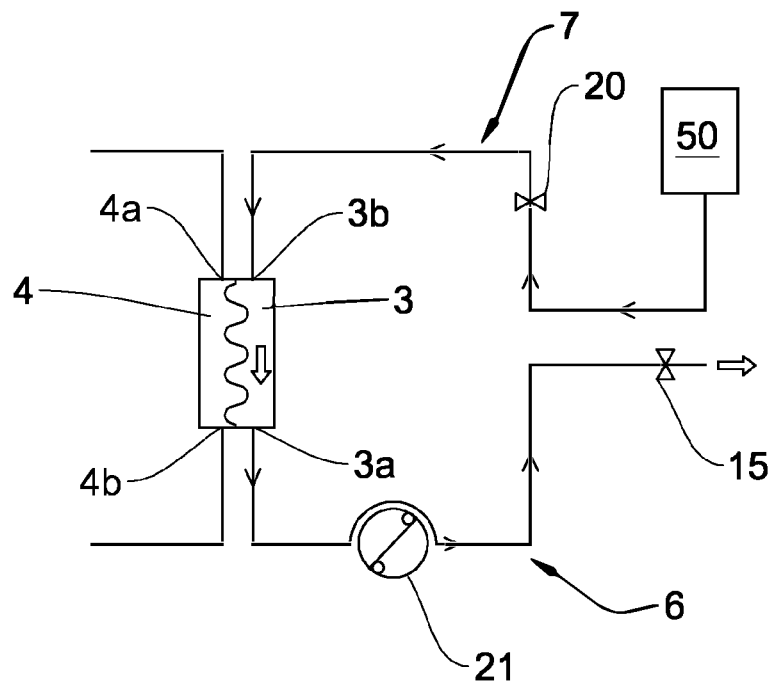
FIGS. 6 and 7 show a schematic representation of the extracorporeal blood treatment apparatus of FIG. 1 in a different priming sequence according to the invention.
Figure 7:
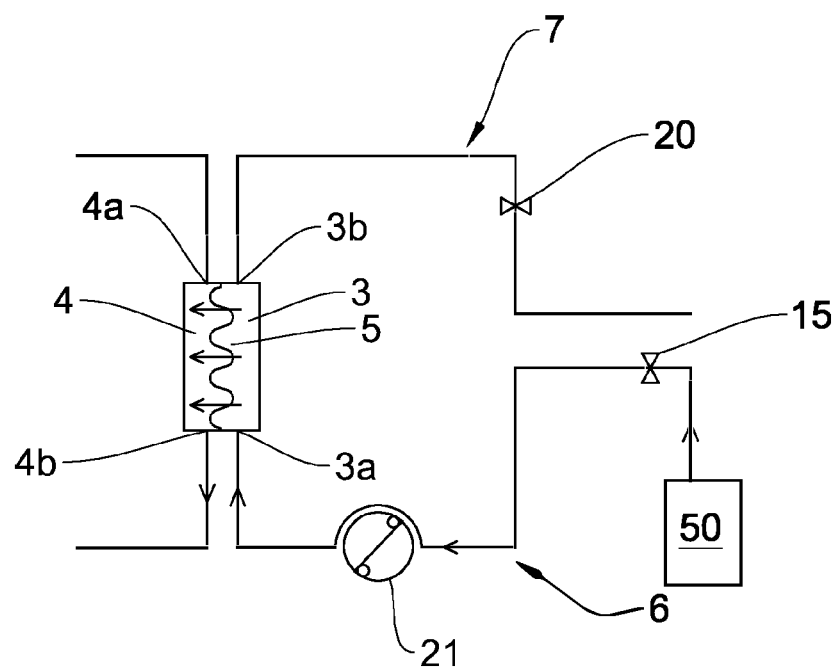

FIGS. 6 and 7 show a different priming sequence, wherein priming the extracorporeal blood circuit 17 includes a first phase of priming the blood withdrawal line 6 and the blood return line 7 and a second subsequent phase. In the first phase, the priming fluid source 50 is connected to the blood return line 7 (FIG. 6). The blood pump 21 is activated to circulate the priming fluid along a reverse circulating direction in the extracorporeal blood circuit 17 while keeping the arterial clamp 15 and the safety valve 20 open. The priming fluid is discharged from the blood withdrawal line 6. In the second phase (FIG. 7), the priming fluid source 50 is connected to the blood withdrawal line 6, the arterial clamp 15 is open, the safety valve 20 is closed and the blood pump 21 is activated to circulate the priming fluid in the blood circuit along a normal circulating direction, thereby pushing the priming fluid through the membrane 5 and priming the fluid chamber 4 with the priming fluid.

Figure 7A:
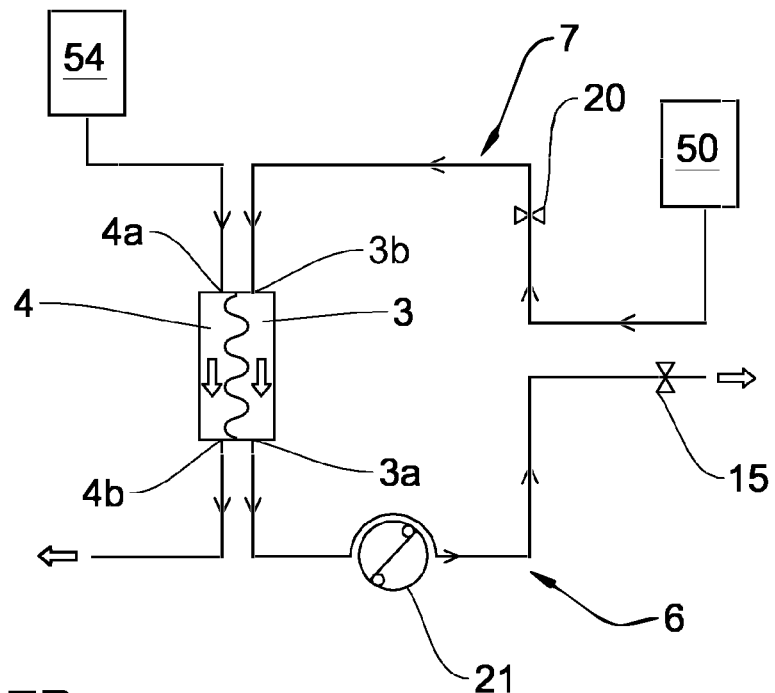
FIG. 7A shows a schematic representation of the extracorporeal blood treatment apparatus of FIG. 1 in a further priming configuration according to the invention.

In a further alternative priming procedure, the priming of the blood circuit is executed according to the previously described embodiments. An auxiliary priming fluid bag 54 is connected to the dialysis side of the circuit (see FIG. 7A). In more detail, the auxiliary priming fluid bag 54 is directly connected to the inlet port 4a of the blood treatment unit 2 by means of an auxiliary priming line. Fluid (e.g., saline) from the auxiliary priming fluid bag 54 is used to prime the fluid chamber 4. This step may be executed at any time during priming operations; however, it is generally performed after priming the blood circuit. A pump of the apparatus (such as the dialysate pump) withdraws fluid from the auxiliary priming fluid bag 54 and make it pass through the fluid chamber 4 to prime it and remove air/air bubbles. The spent fluid is evacuated via a drain (e.g. the machine drain or a drain bag). This alternative priming method avoids back-filtering through the semipermeable membrane.

Figure 7B:
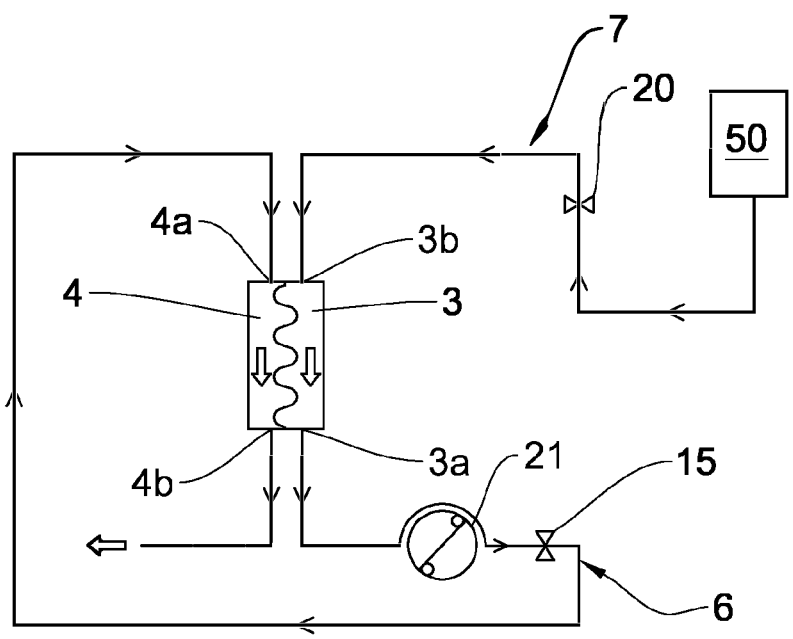
FIG. 7B shows a schematic representation of the extracorporeal blood treatment apparatus of FIG. 1 in a further priming configuration according to the invention.

In a further alternative priming procedure (FIG. 7B), the priming fluid source 50 is connected to the blood return line 7 and the blood withdrawal line 6 is directly connected to the inlet port 4a of the fluid chamber 4 through a tubing (FIG. 7B). The blood pump 21 is activated to circulate the priming fluid along a reverse circulating direction in the extracorporeal blood circuit 17 while keeping the arterial clamp 15 and the safety valve 20 open. The priming fluid flows through the blood chamber 3, out of the inlet port 3a of the blood chamber 3 and then into the fluid chamber 4. Priming fluid than exits from the outlet 4b of the fluid chamber 4 and flows into the effluent line 13.

Once priming of blood chamber and of fluid chamber has been performed, the control unit 12 stops the blood pump 21; the safety valves 15 and 20 are closed. While preparation of the treatment fluid still runs and the fluid preparation device 9 still bypasses the fluid chamber 4 and is not infused in the extracorporeal blood circuit 17, patient P could be connected to the extracorporeal blood circuit 17.

Figure 8A:
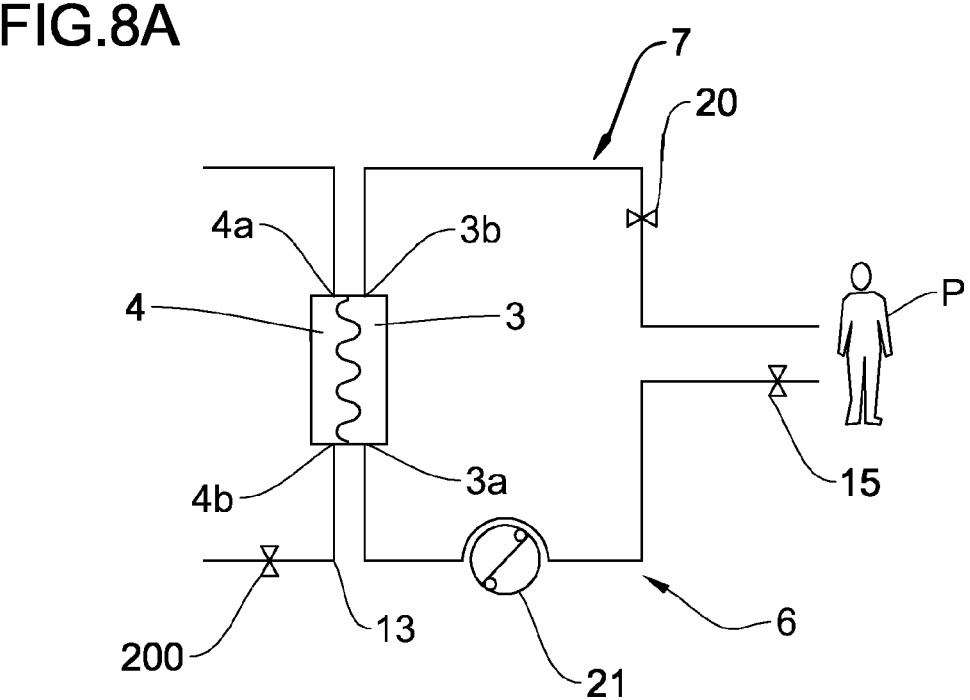
FIGS. 8A and 8B show the connection of a patient to the extracorporeal blood treatment apparatus after priming.
Figure 8B:
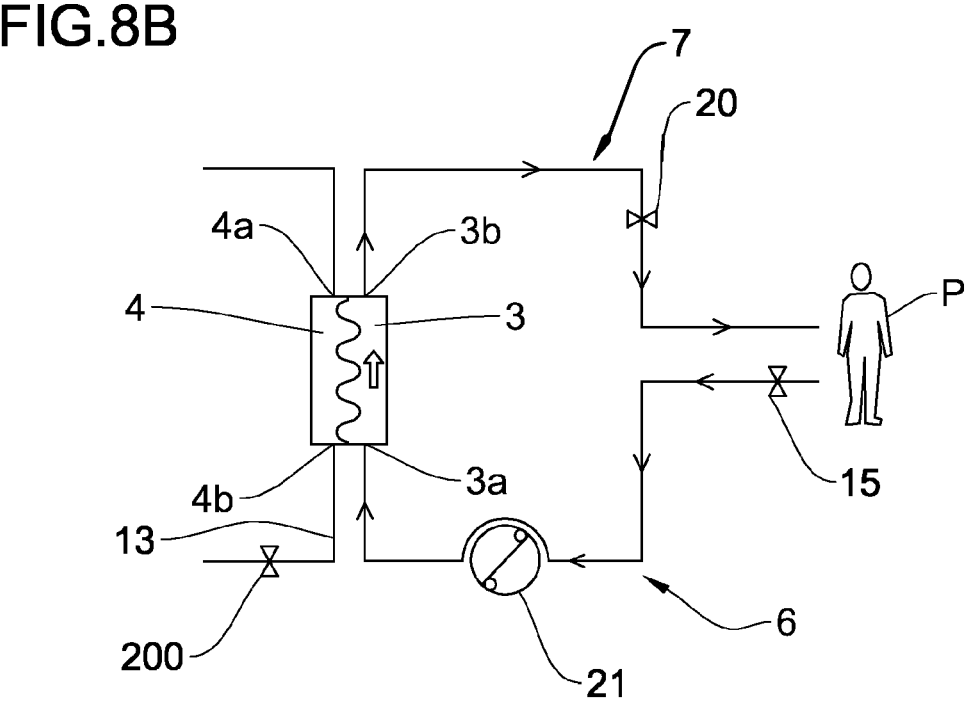

FIGS. 8A and 8B show how the patient P may be connected. The blood withdrawal line 6 and the blood return line 7 are connected to the patient P while the arterial clamp 15 and the safety valve 20 are still closed and an effluent clamp 200 on the effluent line 13 is closed too (FIG. 8A). Then the arterial clamp 15 and the safety valve 20 are opened and the blood pump 21 is activated according to the normal circulating direction while the effluent clamp 200 is still closed (FIG. 8B). Priming fluid in the line is progressively substituted by blood.

Figure 9A:
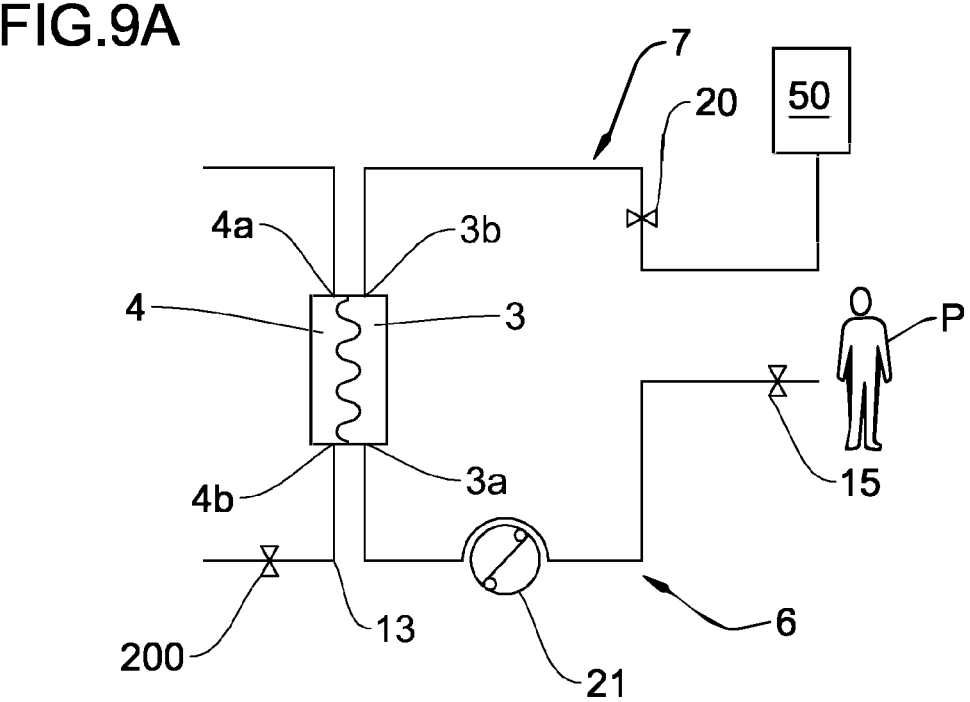
FIGS. 9A and 9B show another way of connecting a patient after priming.
Figure 9B:
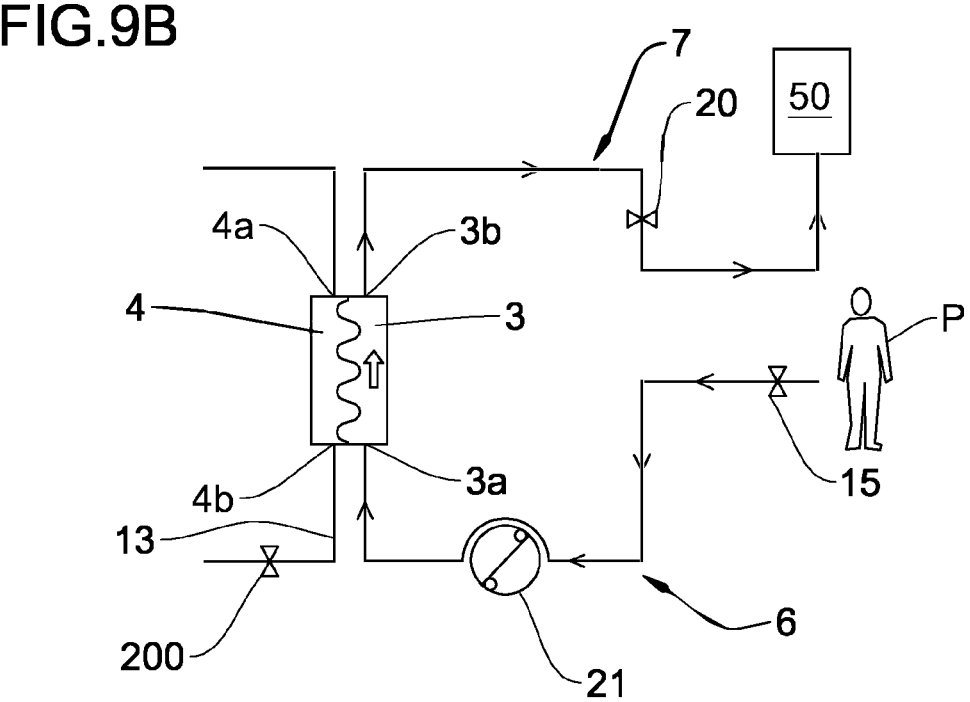

FIGS. 9a and 9b show another way of connecting the patient P. The blood withdrawal line 6 is connected to the patient P while the blood return line is still connected to the priming fluid source/bag 50. The arterial clamp 15, the safety valve 20 and an effluent clamp 200 on the effluent line 13 are closed (FIG. 9A). Then the arterial clamp 15 and the safety valve 20 are opened while the effluent clamp 200 remains closed and the blood pump 21 is activated according to the normal circulating direction (FIG. 9B). Priming fluid in the line is progressively substituted by blood and said priming fluid is collected into the priming fluid source/bag 50 which works as a waste bag. At the end of this step, the blood return line is connected to the patient P.

Figure 4:
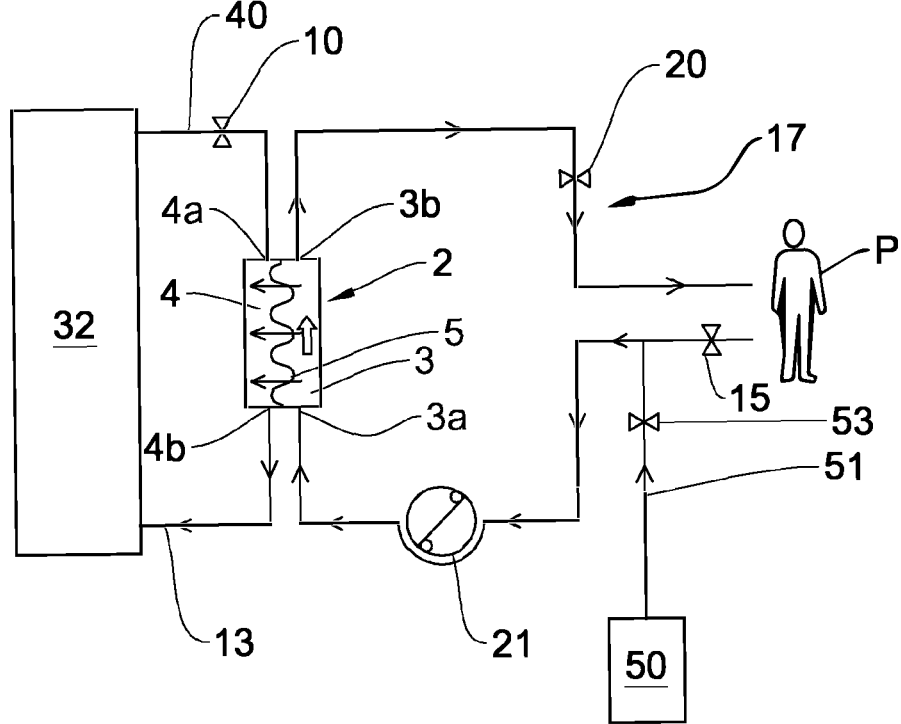

The control unit 12 controls the ultrafiltration device 25, 26 to perform pure ultrafiltration of fluid from the extracorporeal blood of the patient P (FIG. 4). The control unit 12 controls the dialysate pump 26 to pump waste fluid into the evacuation zone 16. Waste fluid removed from blood and crossing the membrane 5 is evacuated through the effluent line 13.

A time interval "$\Delta T_{tfp}$" for treatment fluid preparation may last 20 min. A time interval "$\Delta T_{puhf}$" of the pure ultrafiltration is the difference between the fluid preparation time interval "$\Delta T_{tfp}$" and the priming time interval "$\Delta T_{pr}$" and may be 15 min.

Figure 5:
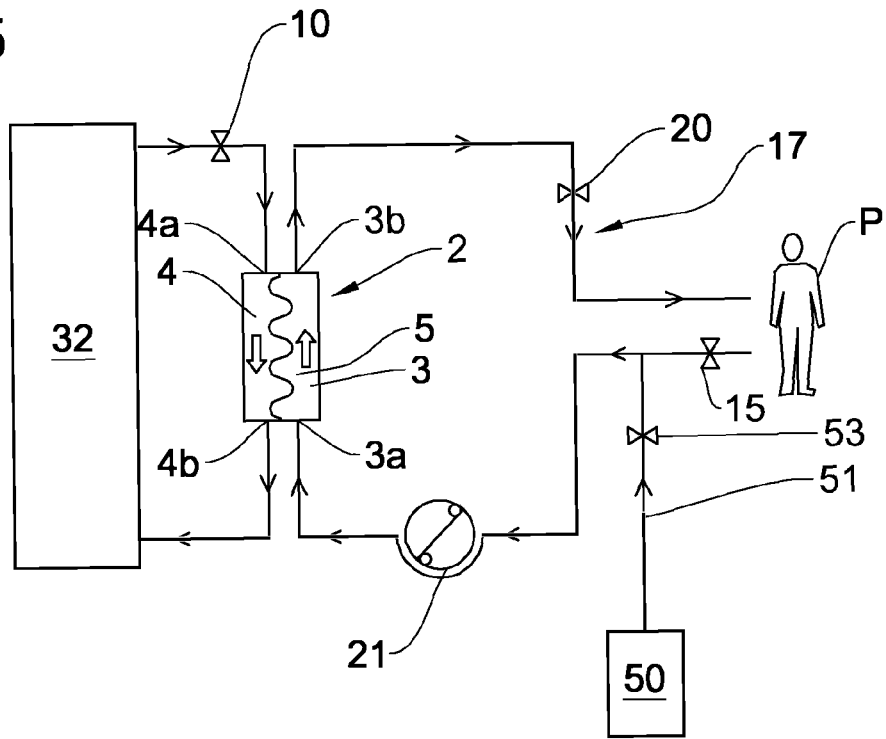

When the treatment fluid is ready for treating the patient blood, i.e. the treatment fluid reached the proper parameter values (temperature, conductivity and/or ion concentration), the control unit 12 raises an alert for the user, in order to require the dialysate connectors to be both placed in the right position at the dialyzer, then controls the fluid check members 24 to restore the fluid connection of the water source 14 and of the treatment fluid preparation device 9 of the treatment fluid circuit 32 to the inlet port 4a of the fluid chamber 4 and/or to the infusion line 43 for injecting substitution fluid in the blood circuit. In a treatment configuration, the control unit 12 controls the treatment fluid pump 25 to pump treatment fluid through the fluid chamber 4 while blood flows in the blood chamber 3 and/or to the infusion line 43. Hemodialysis treatment (or hemodiafiltration treatment or hemofiltration treatment) of the patient P could start (FIG. 5).

In a different way of working, at the starting of the apparatus 1, the apparatus 1 may be configured (or the control unit 12 configures the apparatus to be) simultaneously in the treatment fluid preparation configuration and in the pure UF configuration. In an alternative, after priming the blood line circuit and the fluid chamber and during on-line dialysis fluid preparation, one or more fresh dialysis fluid containers may be connected to the inlet port of the fluid chamber and or to the extracorporeal blood circuit. The control unit could be configured to additionally run an hemodyalisis (HD) treatment flowing fresh dialysis fluid in the fluid chamber and patient blood in the blood chamber or an hemofiltrtion (HF) treatment injecting fresh dialysis fluid in the extracorporeal blood or and hemodiafiltration (HDF) treatment (combining HD and HF) simultaneously with the step of controlling the fluid preparation device to prepare the online dialysis fluid (i.e. change a conductivity and/or an ion concentration of the fluid not having the set conductivity and/or the set ion concentration to prepare the treatment fluid having the set conductivity and/or the set ion concentration). The HD, HF or HDF treatment may be delivered after a pure ultrafiltration initial treatment or as an alternative to the pure ultrafiltration.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and the scope of the appended claims.

The invention claimed is:

1. A method for controlling an extracorporeal blood treatment apparatus with an extracorporeal blood circuit comprising:
setting a hydraulic circuit so that a fluid prepared through a fluid preparation device and not having a set conductivity and/or a set ion concentration bypasses a fluid chamber of a blood treatment device and is not infused in the extracorporeal blood circuit;
controlling the fluid preparation device to change a conductivity and/or an ion concentration of the fluid not having the set conductivity and/or the set ion concentration to prepare a treatment fluid having the set conductivity and/or the set ion concentration while bypassing the fluid chamber and not infusing the fluid in the extracorporeal blood circuit; and
simultaneously controlling an ultrafiltration device of the extracorporeal blood treatment apparatus to perform pure ultrafiltration of fluid from the extracorporeal blood of a patient connected to a blood withdrawal line and to a blood return line of the extracorporeal blood circuit.

2. The method according to claim 1, wherein, in a priming configuration, the apparatus comprises at least one priming fluid source of a priming fluid connected to the extracorporeal blood circuit, to the blood treatment device, or to the hydraulic circuit.

3. The method according to claim 2, comprising, in the priming configuration, priming the extracorporeal blood circuit with the priming fluid before connecting the patient and while the fluid preparation device is preparing the treatment fluid, the priming fluid source connected to the extracorporeal blood circuit.

4. The method according to claim 3, comprising, in the priming configuration, priming the fluid chamber and at least part of the hydraulic circuit with the priming fluid by pushing the priming fluid through a semipermeable membrane from a blood chamber of the extracorporeal blood circuit into the fluid chamber before connecting the patient and while the fluid preparation device is preparing the treatment fluid.

5. The method according to claim 3, comprising, in the priming configuration, priming the fluid chamber and at least part of the hydraulic circuit with a priming fluid from an auxiliary priming fluid source, the auxiliary priming fluid source connected to the blood treatment device or to the hydraulic circuit and separated by a semipermeable membrane from the extracorporeal blood circuit.

6. The method according to claim 1, comprising, in a treatment configuration, connecting the fluid preparation device to the fluid chamber and/or to the extracorporeal blood circuit when the treatment fluid having the set conductivity and/or the set ion concentration is ready for treating the patient blood.

7. The method according to claim 1, comprising, in a treatment configuration, starting a hemodialysis treatment, a hemofiltration treatment, or a hemodiafiltration treatment on the patient when the treatment fluid having the set conductivity and/or the set ion concentration is ready.

8. The method according to claim 1, wherein, the hydraulic circuit comprises a main line having a valve operatively placed between the fluid preparation device and an inlet port of the fluid chamber, the method comprising, in a treatment fluid preparation configuration, closing the valve to set the fluid flowing in the main line downstream the fluid preparation device to bypass the fluid chamber.

9. The method according to claim 8, comprising, in a treatment configuration, when the treatment fluid is ready in order to start a hemodialysis treatment, a hemofiltration treatment, or a hemodiafiltration treatment on the patient, opening the valve to connect the fluid preparation device to the inlet port of the fluid chamber and/or to an infusion line for injecting substitution fluid in the blood circuit.

10. The method according to claim 2, wherein, in the priming configuration, priming the extracorporeal blood circuit includes controlling a blood pump while the priming fluid source is connected to the extracorporeal blood circuit to pump the priming fluid in the extracorporeal blood circuit and to prime the extracorporeal blood circuit with the priming fluid, wherein, in the priming configuration the extracorporeal blood circuit is directly connected to the fluid chamber via a tube, and, the blood withdrawal line is directly connected to the inlet port of the fluid chamber, wherein the blood pump circulates the priming fluid along a reverse circulating direction pumping the priming fluid into the fluid chamber through the tube, in order to prime said fluid chamber and at least part of the hydraulic circuit, and wherein, in the priming configuration, the priming fluid flows through the blood chamber, out of the inlet port of the blood chamber, then into the fluid chamber, exits from the outlet of the fluid chamber, and flows into an effluent line.

11. The method according to claim 2, wherein, the extracorporeal blood treatment apparatus comprises a safety valve placed along the blood return line and an arterial clamp placed along the blood withdrawal line, and wherein, in the priming configuration, priming the extracorporeal blood circuit includes a first phase of priming the blood withdrawal line and the blood return line activating a blood pump to circulate priming fluid along a reverse circulating direction, in the extracorporeal blood circuit and keeping the arterial clamp and the safety valve open and a second phase of closing the safety valve and activating the blood pump to circulate the priming fluid in the blood circuit along a normal circulating direction, thereby pushing the priming fluid through a semipermeable membrane and priming the fluid chamber with the priming fluid.

12. The Method according to claim 11, wherein, the extracorporeal blood treatment apparatus comprises a drain in fluid communication with the fluid chamber and the second phase includes removing air from the fluid chamber through the drain.

13. The method according to claim 1, wherein, the fluid preparation device comprises a conductivity or an ion concentration sensor placed in a main line arranged to sense conductivity or ion concentration of the treatment fluid downstream a concentrate dilution point, and wherein in controlling the fluid preparation device, the method comprises:

receiving the set conductivity and/or the set ion concentration for the treatment fluid;

begin injecting at least one concentrated solution in the main line to increase the conductivity or ion concentration of water flowing in the main line;

receiving from the conductivity or ion concentration sensor a signal indicative of the conductivity or ion concentration of the fluid flowing in the main line; and checking, by means of the conductivity or ion concentration sensor, whether the conductivity or ion concentration of the fluid flowing in the main line has a proper value for treatment of the patient's blood, the proper value being a value within a range around the set conductivity and/or the set ion concentration for the treatment fluid.

14. The method according to claim 1, comprising, in controlling the fluid preparation device:

receiving a set temperature for the treatment fluid;

begin heating water and/or the fluid flowing in a main line; and checking, by means of a temperature sensor, whether the temperature of the fluid flowing in the main line has a proper value for treatment of the patient's blood, the proper value being a value within a range around the set temperature for the treatment fluid.

15. The method according to claim 1, comprising, in a treatment fluid preparation configuration, setting the hydraulic circuit so that the fluid prepared through the fluid preparation device and not having the set conductivity and/or the set ion concentration bypasses the fluid chamber and is not infused in the extracorporeal blood circuit; and controlling the fluid preparation device to change a conductivity and/or an ion concentration of the fluid not having the set conductivity and/or the set ion concentration to prepare the treatment fluid having the set conductivity and/or the set ion concentration while bypassing the fluid chamber and not infusing the fluid in the extracorporeal blood circuit, wherein controlling the fluid preparation device includes starting to inject at least one concentrate solution in water to raise water conductivity and/or ion concentration.

16. The method according to claim 1, comprising, in a pure UF configuration, setting the hydraulic circuit so that the fluid prepared through the fluid preparation device bypasses the fluid chamber and is not infused in the extracorporeal blood circuit; and controlling the ultrafiltration device to perform pure ultrafiltration of fluid from the extracorporeal blood of the patient connected to the extracorporeal blood circuit.

17. The method according to claim 16, comprising, at least at the startup of the apparatus, providing:

simultaneously both a treatment fluid preparation configuration and a priming configuration of the extracorporeal blood treatment apparatus; or simultaneously both the treatment fluid preparation configuration and a pure UF configuration of the extracorporeal blood treatment apparatus.

18. The method according to claim 1, wherein the extracorporeal blood treatment apparatus comprises:

the blood treatment device including a blood chamber and the fluid chamber separated from each other by a semipermeable membrane;

the extracorporeal blood circuit comprising the blood withdrawal line connected to an inlet port of the blood chamber and the blood return line connected to an outlet port of the blood chamber;

a blood pump configured to be coupled to the extracorporeal blood circuit to circulate blood in the extracorporeal blood circuit;

the hydraulic circuit including a main line connectable to an inlet port of the fluid chamber and/or to the extracorporeal blood circuit and an effluent line connected to an outlet port of the fluid chamber, the main line being connectable to a water network to receive water, wherein the hydraulic circuit comprises the fluid preparation device configured to dilute concentrates in water to prepare the treatment fluid having set conductivity and/or set ion concentration;

the ultrafiltration device configured to ultrafilter liquid from the blood chamber towards the fluid chamber of the blood treatment device and to the effluent line; and a control unit connected to the preparation device, to the ultrafiltration device and to the blood pump.

19. A method for controlling an extracorporeal blood treatment apparatus with an extracorporeal blood circuit comprising:

setting a hydraulic circuit so that a fluid prepared through a fluid preparation device and not having a set conductivity and/or a set ion concentration bypasses a fluid chamber of a blood treatment device and is not infused in the extracorporeal blood circuit;

controlling the fluid preparation device to change a conductivity and/or an ion concentration of the fluid not having the set conductivity and/or the set ion concentration to prepare a treatment fluid having the set conductivity and/or the set ion concentration while bypassing the fluid chamber and not infusing the fluid in the extracorporeal blood circuit; and simultaneously, in a priming configuration, priming the extracorporeal blood circuit with a priming fluid before connecting a patient and while the fluid preparation device is preparing the treatment fluid.

20. The method according to claim 19, wherein the fluid preparation device comprises a conductivity or a ion concentration sensor placed in a main line of the hydraulic circuit and arranged to sense conductivity or ion concentration of the treatment fluid downstream a concentrate dilution point, wherein, during controlling the fluid preparation device, the method comprises:

receiving the set conductivity and/or the set ion concentration for the treatment fluid;

begin injecting at least one concentrated solution in the main line to increase the conductivity or ion concentration of water flowing in the main line;

receiving from the conductivity or ion concentration sensor a signal indicative of the conductivity or ion concentration of the fluid flowing in the main line; and checking, by means of the conductivity or ion concentration sensor, whether the conductivity or ion concentration of the fluid flowing in the main line has a proper value for treatment of the patient's blood, the proper value being a value within a range around the set conductivity and/or the set ion concentration for the treatment fluid.

* * * * *